United States Patent
Isomura et al.

(10) Patent No.: US 7,254,985 B2
(45) Date of Patent: *Aug. 14, 2007

(54) OXYGEN SENSOR AND A MANUFACTURING METHOD OF THE SENSOR DEVICE

(75) Inventors: Hiroshi Isomura, Nagoya (JP); Takayoshi Atsumi, Nagoya (JP); Koji Shiono, Nagoya (JP); Masamine Takagi, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 663 days.

This patent is subject to a terminal disclaimer.

(21) Appl. No.: 10/609,553

(22) Filed: Jul. 1, 2003

(65) Prior Publication Data

US 2004/0000480 A1    Jan. 1, 2004

Related U.S. Application Data (62) Division of application No. 09/869,263, filed on Sep. 27, 2001, now Pat. No. 6,672,137.

(30) Foreign Application Priority Data

Oct. 19, 2000   (JP)   ............................. 2000-319651

(51) Int. Cl.
  *G01N 9/00*  (2006.01)
  *G01N 27/26*  (2006.01)

(52) U.S. Cl. .................................. 73/31.05; 204/429
(58) Field of Classification Search ............... 73/31.05, 73/31.06; 204/428, 429
See application file for complete search history.

(56) References Cited

U.S. PATENT DOCUMENTS

| | | | |
|---|---|---|---|
| 3,932,246 A | 1/1976 | Stadler et al. |
| 4,097,353 A | 6/1978 | Kishida et al. |
| 4,249,156 A | 2/1981 | Micheli |
| 4,478,067 A | 10/1984 | Ohta et al. |
| 4,713,646 A | 12/1987 | Sunano et al. |

(Continued)

FOREIGN PATENT DOCUMENTS

EP   0 331 513   9/1989

(Continued)

*Primary Examiner*—Michael Cygan
(74) *Attorney, Agent, or Firm*—Morgan, Lewis & Bockius LLP (57) ABSTRACT

The oxygen sensor of the present invention has excellent durability capable of effectively preventing contamination with lead or the like for a detection electrode even in low temperature exhaust gases, and having stable response over a long period of time. The contamination preventive layer provided in the sensor device comprises composite powders having coarse powders covered therearound with fine powders, and hollows not filled with fine powders are scattered in gaps among the composite powders. Both the coarse and fine powders comprise ceramic powders. Further, it is particularly preferred that the ceramic powders are powders of a titania powder having a peak at 1 μm or less and a composite ceramic powder containing alumina such as spinel having a peak at 10 μm or more. The contamination preventive layer can be formed by coating a slurry containing ceramic powders of different specific surface areas, an organic binder and a solvent such as methanol on the surface of the electrode protection layer followed by drying.

3 Claims, 5 Drawing Sheets

U.S. PATENT DOCUMENTS

| | | |
|---|---|---|
| 5,326,597 A | 7/1994 | Sawada et al. |
| 5,443,711 A | 8/1995 | Kojima et al. |
| 5,538,612 A | 7/1996 | Kojima et al. |
| 5,593,558 A | 1/1997 | Sugino et al. |
| 5,766,434 A | 6/1998 | Fujii et al. |
| 5,849,165 A | 12/1998 | Kojima et al. |
| 6,210,552 B1 | 4/2001 | Mizutani et al. |
| 6,672,137 B1 * | 1/2004 | Isomura et al. ............ 73/31.05 |

FOREIGN PATENT DOCUMENTS

| | | |
|---|---|---|
| EP | 0 369 238 | 5/1990 |
| JP | 55-13828 | 1/1980 |
| JP | 56-035048 | 4/1981 |
| JP | 57-100343 | 6/1982 |
| JP | 61-207961 | 9/1986 |
| JP | 62-14055 | 1/1987 |
| JP | 1-227955 | 9/1989 |
| JP | 2-47546 | 2/1990 |
| JP | 4-164244 | 6/1992 |
| JP | 404335149 | 11/1992 |
| JP | 6-174683 | 6/1994 |
| JP | 6-90176 | 11/1994 |
| JP | 9-54064 | 2/1997 |
| JP | 9-113480 | 5/1997 |
| JP | 10-221296 | 8/1998 |
| JP | 11-83789 | 3/1999 |

* cited by examiner

OXYGEN SENSOR AND A MANUFACTURING METHOD OF THE SENSOR DEVICE

This is a divisional of application Ser. No. 09/869,263 filed on Sep. 27, 2001 now U.S. Pat. No. 6,672,137.

FIELD OF THE INVENTION

This invention concerns an oxygen sensor comprising a sensor device for detecting an oxygen density and a method of manufacturing the sensor device.

BACKGROUND OF THE INVENTION

When a oxygen sensor comprising a sensor device is exposed as an air/fuel ratio sensor to an exhaust gas upon using lead-containing fuels, electrodes are contaminated with lead, phosphorus, silicon or the like and degraded with lapse of time to no more provide sufficient electromotive force. Sensors coping with the problem of deterioration for the durability of electrodes are disclosed, for example, in Japanese Patent Publication No. 90176/1994 and Japanese Laid-Open No. 113480/1997. However, a sensor capable of completely preventing contamination to electrodes in a low temperature region which is most likely to undergo the effect of lead or the like contained in exhaust gases has not yet been obtained.

This invention intends to provide an oxygen sensor having a sensor device capable of preventing an electrode from contamination by lead or the like and having excellent durability even in contact with exhaust gases at a relatively low temperature, as well as a method of manufacturing such a sensor device.

DISCLOSURE OF THE INVENTION

The oxygen sensor of the present invention is an oxygen sensor comprising a sensor device including a detection electrode, an electrode protection layer formed on the surface of the detection electrode and a contamination preventive layer formed on the surface of the electrode protection layer, wherein the contamination preventive layer comprises a composite powder having a ceramic powder having a large grain size (referred to hereinafter as coarse powder) covered therearound with a ceramic powder having a small grain size (referred to hereinafter as fine powder), and hollows not filled with the fine powder are scattered in gaps among such composite powders.

By forming the contamination preventive layer as described above, contamination materials are trapped by the fine powder and prevented from reaching the electrode in the oxygen sensor, thus preventing a deterioration by contamination in the performance of the oxygen sensor. On the other hand, the fine powder is carried on the coarse powder, thus preventing the problem of removal of a contamination preventive layer from a sensor device surface such as a layer composed exclusively of the fine powder upon high heat setting during continuous use at high temperatures. Further, the fine powder is carried so as to cover the surface of the coarse powder, while suitable hollows having a similar size to that of the coarse powder are formed in gaps among the coarse powders, so that the gaps among the coarse powders are not completely filled with the fine powder, and therefore, the contamination preventive layer cannot be clogged even upon accumulation of contamination materials thereon, to prevent a reduction in the response of the sensor.

The grain size distribution of primary particles of the ceramic powder constituting the contamination preventive layer as described above has at least two peaks, and if the peak on the side of the smallest grain size is 10 µm or less and the peak on the side of the largest grain size is 0.1 µm or more, a desirable contamination preventive layer having a high contamination preventing effect is given.

In this case, the peak on the side of the small grain size is preferably at 1 µm or less and can be at 0.05 µm or less and, particularly, at 0.01 µm or less. Further, the peak on the side of the large grain size is preferably at 1 µm or more and can be, particularly, 10 µm or more.

For good biting of the coarse particle, the electrode protection layer under the contamination preventive layer is formed preferably by spray coating.

The "ceramic powder" contained in the "contamination preventive layer" is preferably selected from the powder of oxide which is chemically stable in exhaust gases at high temperature such as titania, alumina, silica, and composite oxide containing aluminum atoms such as spinel and mullite. Powder other than the oxide may also be used so long as it is chemically stable. In this case, two or more kinds of ceramic powders of different compositions may be mixed. When the ceramic powder in one composition is a fine powder while the ceramic powder in the other composition is a coarse powder, the degree of freedom is extended in the selection of the powder to facilitate the provision of the powder having a desired grain size distribution, and such ceramic powders can be used conveniently by selecting a ceramic powder having a high contamination-preventing effect as the fine powder and a ceramic powder having high-temperature durability as the coarse powder.

The two or more kinds of ceramic powders of different compositions, preferably, contain a titania powder having a peak in the grain size distribution at 1 µm or less and a ceramic powder other than titania having a peak in the grain size distribution at 10 µm or more.

Titania is considered to be excellent in the ability to adsorb contamination materials. In particular, anatase type titania can be used for easily providing a powder having a small grain diameter and a high contamination preventing effect.

Preferred ceramic powder other than titania is, particularly, less heat shrinkable ceramic powder such as a composite oxide containing aluminum atoms such as spinel or mullite.

Further, a titania powder having a peak from 0.003 to 0.5 µm is combined particularly preferably with a ceramic powder other than titania having a peak from 15 to 50 µm in order to form suitable gaps in the contamination preventive layer. Such powders can be incorporated to provide a contamination preventive layer which can sufficiently adsorb contamination materials, is not removed by thermal shrinkage from the electrode protection layer and is further superior in durability with less drop in response.

Figure 1:
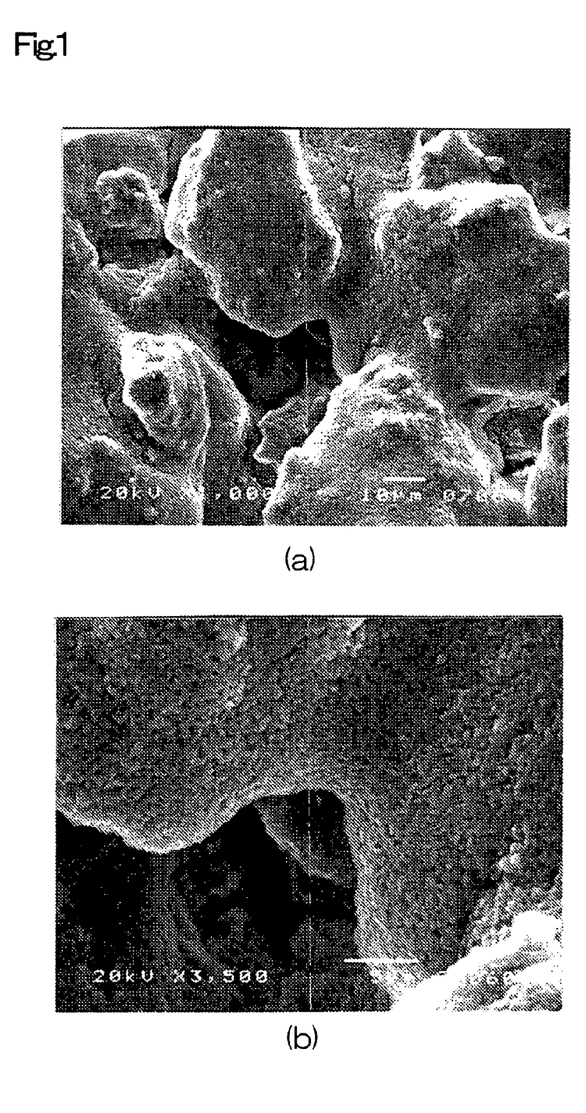

That is, when a powder having a peak of small grain sizes in the range of 1 µm or less, preferably 0.003 to 0.5 µm is used in combination with a powder having a peak of large grain sizes in the range of 10 µm or more, preferably 15 to 50 µm, the contamination preventive layer as shown in FIGS. 1(a) & (b) having suitable hollows with a similar size to that of coarse powder therein is formed from composite powders comprising a large number of particles of the powder with small grain sizes adhering to the surfaces of particles of the powder having large grain sizes, so the contamination preventive layer can sufficiently keep air-permeability, can certainly adsorb contamination materials, and can be rendered highly durable.

As the coarse powder and fine powder, powders identical in the composition but different in the crystal phase can also be selected. It is particularly preferable that an anatase type titania powder is used as the fine powder and a rutile type titania powder as the coarse powder. Both powders are titania powders but are different in the crystal phase, and these are provided as fine and coarse powders having a narrow distribution of grain sizes and are thus suitable for forming a contamination preventive layer excellent in air-permeability. For the contamination preventive effect, the grain diameter in the peak of the grain size distribution of the anatase type titania powder is preferably 0.5 μm or less, more preferably in the range of 0.003 to 0.5 μm. For the contamination preventive effect, the grain diameter in the peak of the grain size distribution of the rutile type titania powder is preferably 1 μm or more, more preferably in the range of 3 to 8 μm. By combination of the anatase type titania powder having a very small grain diameter of about 0.003 to 0.5 μm with the rutile type titania having a larger grain size, the contamination preventive layer excellent in the action of capturing poisoning materials can be formed. Further, by using the ceramic powders having the same composition, the composite powders can be easily formed to provide the contamination preventive layer with a good contamination preventing effect.

When the grain size distribution of the contamination preventive layer in the product is evaluated, the grain size can be read in the field of view of an electronic microscope on one hand, or from a photograph thereof. When the grain size is read from the field of view of the electronic microscope or from its photograph, each of the primary grains that can be confirmed visually is measured for the diameter of circumcircle and determined as a grain size. Measurement for the grain size is conducted for a plurality of primary particles (about 1000) to calculate the grain size distribution. In a case of using oxide powders of different compositions, the grain size can be measured to determine the grain size distribution on the oxide powder of each of the compositions. However, in view of the gist of this invention, when the grain size is measured in a mixed state of the fine grain powder and the coarse grain powder, it is not necessary to measure the grain size distribution on every ceramic powders of different compositions but the grain size distribution may be measured using grain size diameter sampled at random from the contamination preventive layer. As a result, it may suffice that the peak on the side of the small grain size is 1 μm or less and the peak on the side of the large grain size is 0.1 μm or more.

On the other hand, grain size distribution of the fine grain powder is sometimes difficult to measure using a usual scanning type electron microscope or the like and it can be measured in the same manner as described above by using an electron microscope of high resolution power, but it can also be calculated according to the Scheller's equation by using an X-ray small angle scattering method for measuring the grain size distribution of the powder.

In addition, the grain size distribution can also be measured by a generally utilized method such as a laser beam diffraction method or centrifugal precipitation method. However, it is often difficult to measure the grain size distribution for an identical sample from a fine region to a coarse region by an identical measuring method. In such a case, the grain size distribution in the fine region and the coarse region may be measured by different measuring methods and the grain size distribution in the contamination preventive layer may be identified based on the respective grain size distributions.

The method of manufacturing the sensor device in the oxygen sensor of the present invention comprises kneading one or more kinds of first ceramic powders, one or more kinds of second ceramic powders with a peak of a grain size distribution of primary particles being on the side of a large grain size than the peak of a grain size distribution of primary particles of the first ceramic powder whereupon the difference between the maximum grain diameter of 10% particles on the side of a small grain diameter (referred to hereinafter as 10% grain diameter or d10) and the maximum grain diameter of 90% particles on the side of a small grain diameter (referred to hereinafter as 90% grain diameter or d90) is not more than twice of the grain diameter as the peak value of the grain size distribution, an organic binder and a solvent to prepare a contamination preventive layer-forming paste, coating said contamination preventive layer-forming paste on the surface of the electrode protection layer of an oxygen sensor device to form a coating and subsequently heating and drying said coating thereby forming the contamination preventive layer. According to this method, a powder having a regular grain diameter near to a peak in the distribution of grain sizes is used as the second ceramic powder serving as a coarse powder in the contamination preventive layer, thus facilitating formation of the contamination preventive layer having hollows with a similar size to that of the coarse powder scattered therein. Further, by incorporating an inorganic binder suitably into the contamination preventive layer-forming paste, the fine powder can adhere to the surface of the coarse powder to achieve an excellent contamination preventive layer. Further, the first ceramic powder serving as the fine powder and the second ceramic powder as the coarse powder are preferably highly heat-resistant oxides.

In particular, a titania powder or the like having a specific surface area of 2 to 500 $m^2/g$ can be used as the first ceramic powder and an aluminum atom-containing composite oxide powder or the like having a specific surface area of 0.1 to 100 $m^2/g$ as the second ceramic powder. Alternatively, an anatase type titania powder having a specific surface area of 2 to 500 $m^2/g$ is used as the first ceramic powder and a rutile type titania powder having a specific surface area of 0.1 to 10 $m^2/g$ as the second ceramic powder, and from these powders, the contamination preventive layer can also be formed in an analogous manner.

The specific surface area of the first ceramic powder is 2 to 500 $m^2/g$, particularly preferably 5 to 300 $m^2/g$. If the specific surface area is less than 2 $m^2/g$, the resulting contamination preventive layer is deteriorated in both physical capture of contamination materials and reaction therewith, while if the specific surface area is greater than 500 $m^2/g$, the powders easily aggregate and their reactivity with contamination materials becomes too high, and the response of the resulting oxygen sensor gradually changes unfavorably under a high-temperature environment. On the other hand, the specific surface area of the second ceramic powder is 0.1 to 100 $m^2/g$, particularly preferably 0.3 to 10 $m^2/g$. If the specific surface area is less than 0.1 $m^2/g$, a uniform contamination preventive layer having a smooth surface cannot be formed, while it is higher than 100 $m^2/g$, the contamination preventive layer cannot be sufficiently prevented from being aggregated. When the specific surface area of the second ceramic powder is in the range described above, hollows are formed and dispersed in gaps among coarse powders, to provide the contamination preventive layer with good air-permeability.

The specific surface area can be determined according to the BET method. Further, when the specific surface area of the powder is particularly large, it can be measured by using a full automatic surface area measuring apparatus, Model "Multisoap 12" manufactured by Yuasa Ionics Co.

The first and second ceramic powders are preferably contained in amounts of at least 15 parts by weight (referred to hereinafter as "parts") respectively relative to 100 parts of the contamination preventing layer forming paste. If the content of either the first or second ceramic powder in particular of the first ceramic powder is less than 15 parts, contamination materials cannot be sufficiently captured. Further, if the content of the second ceramic powder is less than 15 parts, suitable hollows cannot be formed among the coarse powders in the contamination preventive layer, thus failing to maintain the air-permeability. For forming suitable hollows in the contamination preventive layer, both the first and second ceramic powders are more preferably contained in amounts of 20 to 50 parts respectively. In the ceramic powder, other ceramic powder than each of the powders as the essential constituent factors of this invention can also be mixed, but mixing of the ceramic powder whose grain size distribution for the entire ceramic powder is out of the gist of this invention is not preferred.

Further, the ratio of the mixing amount between the first ceramic powder and the second ceramic powder is not particularly restricted but it is preferred to mix 100 parts of one of them and from 40 to 250 parts, particularly, 80 to 130 parts of the other of them and they may be mixed about in an equal amount. If there is no significant difference in the ratio of the amount of the powders, a homogeneous contamination preventive layer excellent in the function of trapping the contamination substances and having smooth surface can be formed more efficiently.

The "contamination preventive layer-forming paste" is obtained by kneading the ceramic powders, an organic binder and a solvent such as methanol, xylene etc. and a suitable inorganic binder or the like. The coating film formed on the surface of the electrode protection layer is solidified and hardened sufficiently by drying at 100 to 150° C. for about 5 to 20 min, after the drying, attaching the sensor device with the dried coating film to a protection tube receptacle, and then heating the sensor device in an assy furnace which is controlled for temperature 300-700° C., particularly, to about 400-600° C. in a reducing atmosphere for about 20 to 60 min., and then a sensor device provided with a contamination preventive layer having predetermined contamination preventive function and thickness can be formed.

The thickness of the contamination preventive layer shall be 50 to 300 μm, particularly preferably 150 to 250 μm. If its thickness is too small, contamination materials may not be sufficiently captured. On the other hand, if it exceeds 250 μm, it is not preferred since the response of the oxygen sensor obtained is lowered and, further, the contamination preventive layer tends to be exfoliated from the electrode protection layer.

BRIEF DESCRIPTION OF THE DRAWINGS

FIG. 1 (a) is a scanning type electron microscopic photograph in the magnification factor of 1000× for a contamination preventive layer formed to a sensor device of an Experimental Example 20. (b) is a scanning type electron microscopic photograph at a magnifying factor of 3500× that magnifies a central portion for (a).

PREFERRED EMBODIMENTS OF THE INVENTION (1) Preparation of Oxygen Sensor

After adding 5 mol % of yttria at 99.9% purity to zirconia at a purity of 99% or higher and wet mixing them, they were calcined at 1300° C. for 2 hours. Then, water was added and wet pulverization was conducted by using a ball mill till 80% of particles were decreased to a grain size of 2.5 μm or less and then a water soluble binder was added and they were prepared by a spray drier method into a spherical powder with an average grain size of 70 μm.

A predetermined molding product of a bottomed cylindrical shape was obtained using the powder by a rubber press method, which was dried and ground with a grinding stone to arrange the shape. Subsequently, a slurry prepared by adding a water soluble binder and water to the powder was deposited on the outer surface of the molding product and dried. Then, it was sintered being maintained at 1500° C. for 2 hours to prepare a solid electrolyte substrate. Then, a platinum electrode of 1 to 2 μm thickness exposed to a gas to be detected such as an exhaust gas is formed by electroless plating to prepare a detection electrode. Then, a platinum electrode of 1 to 2 μm thickness to be exposed to atmospheric air was disposed by electroless plating to form a reference electrode. Then, a heat treatment was applied in an atmospheric air at 1200° C. for one hour to improve the denseness of the detection electrode. Subsequently, a spinel powder ($MgAl_2O_4$) was coated on the surface of the detection electrode to form an electrode protection layer.

Then, powder ① and powder ② of the kind and the ratio of amount as described in Table 1 and 2, as well as a predetermined amount of a solvent and an alumina sol were mixed in a pot mill using nylon balls to prepare a slurry. Based on 100 mass % of the slurry, the total amount for the powders ① and ② was 70, methanol containing an organic binder was 23 mass % and the alumina sol was 7 mass % in Experimental Examples 1 to 9, the total amount for the powders ① and ② was 50 mass %, water was 40 mass % and the alumina sol was 10 mass % in Experimental Examples 10 to 15, the total amount for the powders ① and ② was 56 mass %, water was 35 mass % and the alumina sol was 9 mass % in Experimental Examples 16 to 30. Subsequently, substrates formed with the electrode protection layers were immersed in the slurry to form coating films on the surface of the electrode protection layers, and dried at 120° C. to form contamination preventive layers of 50 to 300 μm thickness (desirably 150 to 250 μm) to prepare sensor devices. Then, after assembling the sensor devices to protection tube receptacles, for instance, they were heated at 500° C. to obtain oxygen sensors.

taining 0.4 g of lead per one liter was used as the fuel. An application voltage to a heater for heating the oxygen sensor

TABLE 1

| Experimental Example | Powder (1) Powder species | Powder (1) Peak value for grain size distribution (μm) | Powder (1) Addition amount (wt %) | Powder (2) Powder species | Powder (2) Peak value for grain size distribution (μm) | Powder (2) Addition amount (wt %) | Appearance of poisoning preventive layer | Poisoning resistance |
|---|---|---|---|---|---|---|---|---|
| 1 | Anatase type titania with peak value of 0.02 μm | | 30 | Anatase type titania with peak value of 0.08 μm | | 40 | Viscosity of slurry excessively high and not usable | |
| 2 | Anatase type powder (St-01) | 0.01 | 0 | Rutile type powder (NS-90) | 5 | 70 | ○ | X (response degraded greatly) |
| 3 | | | 10 | | 7 | 60 | ○ | Δ (response degraded) |
| 4 | | | 20 | | 6 | 50 | ○ | ○ |
| 5 | | | 30 | | 5 | 40 | ○ | ○ |
| 6 | | | 40 | | | 30 | ○ | ○ |
| 7 | | | 50 | | 7 | 20 | ○ | ○ |
| 8 | | | 60 | | 5 | 10 | Δ (cracked product presence) | ○ (evaluated only those with no crack) |
| 9 | | | 70 | | 5 | 0 | X (crack formed entire specimen) | - (not measurable) |
| 10 | | | 0 | Spinel type powder (SMJ-214) | 43 | 50 | ○ | X (response degraded greatly) |
| 11 | | | 9 | | 43 | 41 | ○ | Δ (response degraded) |
| 12 | | | 17 | | 24 | 33 | ○ | ○ |
| 13 | | | 25 | | 34 | 25 | ○ | ○ |
| 14 | | | 33 | | 15 | 17 | ○ | ○ |
| 15 | | | 51 | | 15 | 0 | X (crack formed entire specimen) | - (not measurable) |

TABLE 2

| Experimental Example | Powder (1) Powder species | Powder (1) Peak value for grain size distribution (μm) | Powder (1) Addition amount (wt %) | Powder (2) Powder species | Powder (2) Peak value for grain size distribution (μm) | Powder (2) Addition amount (wt %) | Appearance of poisoning preventive layer | Poisoning resistance |
|---|---|---|---|---|---|---|---|---|
| 16 | Rutile type titania with peak value of 8 μm | | 28 | Spinel powder with mean peak value of 30 μm | | 28 | ○ | X (response degraded greatly) |
| 17 | Anatase type powder (St-41) | 0.2 | 0 | Rutile type powder (NS-90) | 43 | 56 | ○ | X (response degraded greatly) |
| 18 | | 0.2 | 4 | | 43 | 52 | ○ | Δ (response degraded) |
| 19 | | 0.4 | 12 | | 24 | 44 | ○ | |
| 20 | | 0.3 | 20 | | 15 | 36 | ○ | ○ |
| 21 | | 0.2 | 28 | | 34 | 28 | ○ | ○ |
| 22 | | 0.3 | 34 | | 28 | 20 | ○ | ○ |
| 23 | | 0.3 | 56 | | 28 | 0 | X (crack formed entire specimen) | - (not measurable) |
| 24 | | 0.2 | 0 | | 5 | 56 | ○ | X (response degraded greatly) |
| 25 | | 0.2 | 4 | Spinel type powder (SMJ-214) | 7 | 52 | ○ | Δ (response degraded) |
| 26 | | 0.4 | 12 | | 6 | 44 | ○ | |
| 27 | | 0.3 | 20 | | 5 | 36 | ○ | ○ |
| 28 | | 0.2 | 28 | | | 28 | ○ | ○ |
| 29 | | 0.3 | 34 | | 7 | 20 | ○ | ○ |
| 30 | | 0.3 | 56 | | 5 | 0 | X (crack formed entire specimen) | - (not measurable) |

(2) Evaluation for the Performance of the Oxygen Sensor
(1) Appearance of the Contamination preventive layer The appearance of the contamination preventive layer of the oxygen sensor obtained in (1) was visually observed.

The evaluation standards ○: surface was smooth with no cracks being observed, Δ: cracks formed partially, X: cracks formed in entire samples.

[2] Contamination Resistance (Durability)

Figure 6:
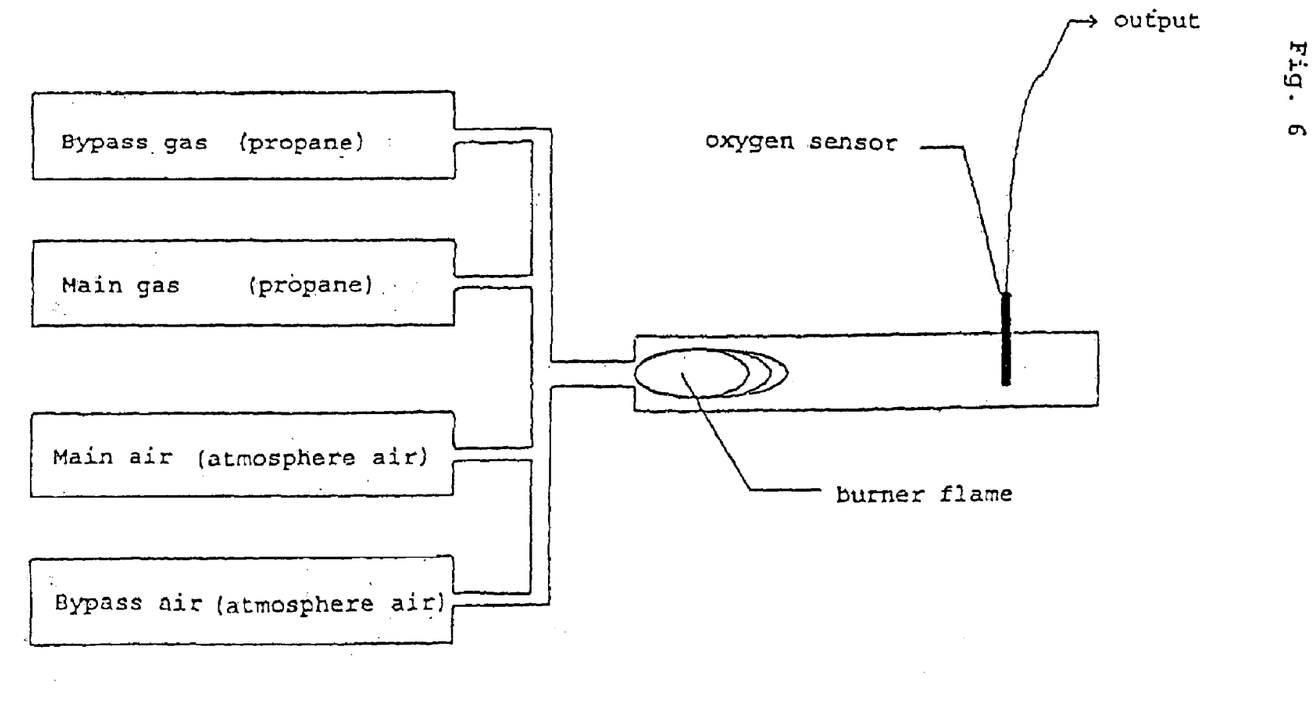
FIG. 6 is a schematic view for a burner measuring apparatus for evaluating the durability.

1800 cc engine was used and an endurance pattern was taken according to a life cycle pattern. Lead gasoline containing 0.4 g of lead per one liter was used as the fuel. An application voltage to a heater for heating the oxygen sensor was set to 14 V for stabilizing detection function. The sensor attaching position was at a position nearer to an engine where exhaust gases at a high temperature of 500 to 800° C. were passed and at a position remote from the engine where low temperature exhaust gases at 350° C. to 700° C. were passed. After conducting duration test for 100 hours in this way, the performance of the lead durability for each of the oxygen sensors was evaluated using an apparatus shown schematically in FIG. 6 by a burner measuring method.

The evaluation standards ○: response scarcely deteriorated, Δ: response deteriorated but not out of the control value in air/fuel cost control, X: response deteriorated greatly and out of the control value upon air/fuel cost control.

Result of Experiments

According to the result in Table 1, it can be seen that the surface of the contamination preventive layer is smooth, no cracks being observed at all and both the high temperature durability and low temperature durability are excellent in Experimental Example 3 to 8 and 11 to 14 where the powder ① as the fine grain powder and the powder ② as the coarse grain powder are within the preferred range of the invention described in one embodiment. Further, it was observed that hollows having a similar size to that of the coarse powder are scattered in the inside of the contamination preventive layer. Further, the viscosity of the slurry was excessively high and the coating film forming the contamination preventive layer could not be formed in Experimental Example 1 where peak values for the powders ① and ② is (each) less than 0.1 μm. Further, the durability was deteriorated greatly in Experimental Example 3 where the powder ① was not contained, and cracks were formed in the entire samples and they could not be put to practical use in 9 and 15 where powder ② was not contained Further in Experimental Examples 3 and 11 where the ratio of the powder ① is low, the outward appearance was good, but the durability of the resulting contamination preventive layer tended to be deteriorated because the surface of the coarse powder was not sufficiently covered with the fine powders. Further in Experimental Example 8 where the ratio of the powder ① is high, some products were observed to have cracks on the surface of the contamination preventive layer. However, the cracking-free products were durable to show good performance.

According to the result in Table 2, it can be seen that the surface of the contamination preventive layer was smooth and cracks were not observed at all in Experimental Examples 18 to 22 and Experimental Examples 25 to 29 within a preferred range of this invention where the peak value in the grain size distribution for the powder ① as the fine grain powder was larger compared with the case in Table 1. Further, in Experimental Examples 18 to 22 and Experimental Examples 25 to 29, contamination resistance was also good since the amounts of the powder ① and the powder ② were within a preferable range. Further, the durability was deteriorated greatly since the grain is excessively large in Experimental Example 16 where the both of the peak values for the powders ① and ② exceeded 10 μm. Further, durability was deteriorated greatly also in Experimental Examples 17 and 24 where the powder ① was not contained, and cracks were formed in the entire samples and they could not put to practical use in 23 and 30. Further in Experimental Examples 18 and 19 where the ratio of the powder ① is low, the outward appearance was good, but the durability of the resulting contamination preventive layer tended to be deteriorated because the surface of the coarse powder was not sufficiently covered with the fine powders. Further in Experimental Examples 31 and 32 where the grain-size distribution of the powder ② has a relatively broader grain-size distribution than the desired range in the present invention, the contamination preventive layer was free of cracking during manufacturing because suitable hollows were not formed, but it was poor in contamination resistance to show a change in the response of the sensor depending on contamination materials.

EXAMPLE 1

A paste was prepared by stirring and mixing 20 g of an anatase type titania powder having a specific surface area of 10 $m^2/g$ with a peak in the grain size distribution at 0.2 μm, 20 g of spinel powder having a specific surface area of 0.5 $m^2/g$ with a peak in the grain size distribution at 34 μm, 28 g of water and 3 g of an alumina sol as the starting materials in a pot mill for 2 hours using nylon balls. Subsequently, a sensor device having an electrode protection layer prepared in (1) was dipped into the paste, the paste was coated by about 100 mg on the surface of the electrode protection layer and dried at 120° C. for 10 min to form a contamination preventive layer of from 150 to 250 μm thickness, to prepare a sensor device. Then, after assembling the same to a protection tube receptacle for instance, it was heated at 500° C. for 30 min to obtain an oxygen sensor.

The contamination preventive layer thus formed was smooth and cracks were not observed at all. Then, it was observed that the contamination preventive layer was formed in such a state that the surface of the coarse powder was sufficiently covered with the fine powders, and further that hollows of a similar size to that of the coarse powder were scattered in the inside of the contamination preventive layer. Further, as a result of evaluation in the same manner as in (2), ②, it was confirmed that both the high temperature durability and low temperature durability were extremely excellent. Further, an oxygen sensor incorporated with the sensor device having the contamination preventive layer (product of the embodiment) or an oxygen sensor incorporated with a sensor device formed with a contamination preventive layer using a ceramic powder not containing fine grain powder (Experimental Example 17 in Table 2) (Comparative Product) were exposed to exhaust gases formed from fuels with addition of a predetermined amount of silicon for a long period of time and then the sensors were attached to an engine and evaluated for the response. As a result, it was found that while the response was lowered considerably with lapse of time in the comparative product, delay in the response was reduced in the product of the embodiment. Further, according to the X-ray powder diffraction pattern for the contamination preventive layer, crystal phases for the anatase type titania, spinel and alumina were observed.

EXAMPLE 2

After paste was obtained in the same manner as in Example 1 except for using 22.5 g of an anatase type titania powder having a specific surface area of 500 $m^2/g$ with a peak in the grain size distribution at 0.007 μm, 22.5 g of a rutile type titania powder having a specific surface area of 0.7 $m^2/g$ with a peak in the grain size distribution at 7 μm, 35 ml of methanol and 2.8 g of alumina sol as the starting materials, a sensor device having the electrode protection layer prepared in (1) was dipped into the paste, the paste was coated by about 100 mg on the surface of the electrode protection layer and dried at 120° C. for 10 min to form a contamination preventive layer of from 150 to 250 μm thickness, to prepare a sensor device. Then, after assembling the same to a protection tube receptacle for instance, it was heated at 500° C. for 30 min to obtain an oxygen sensor.

Figure 2:
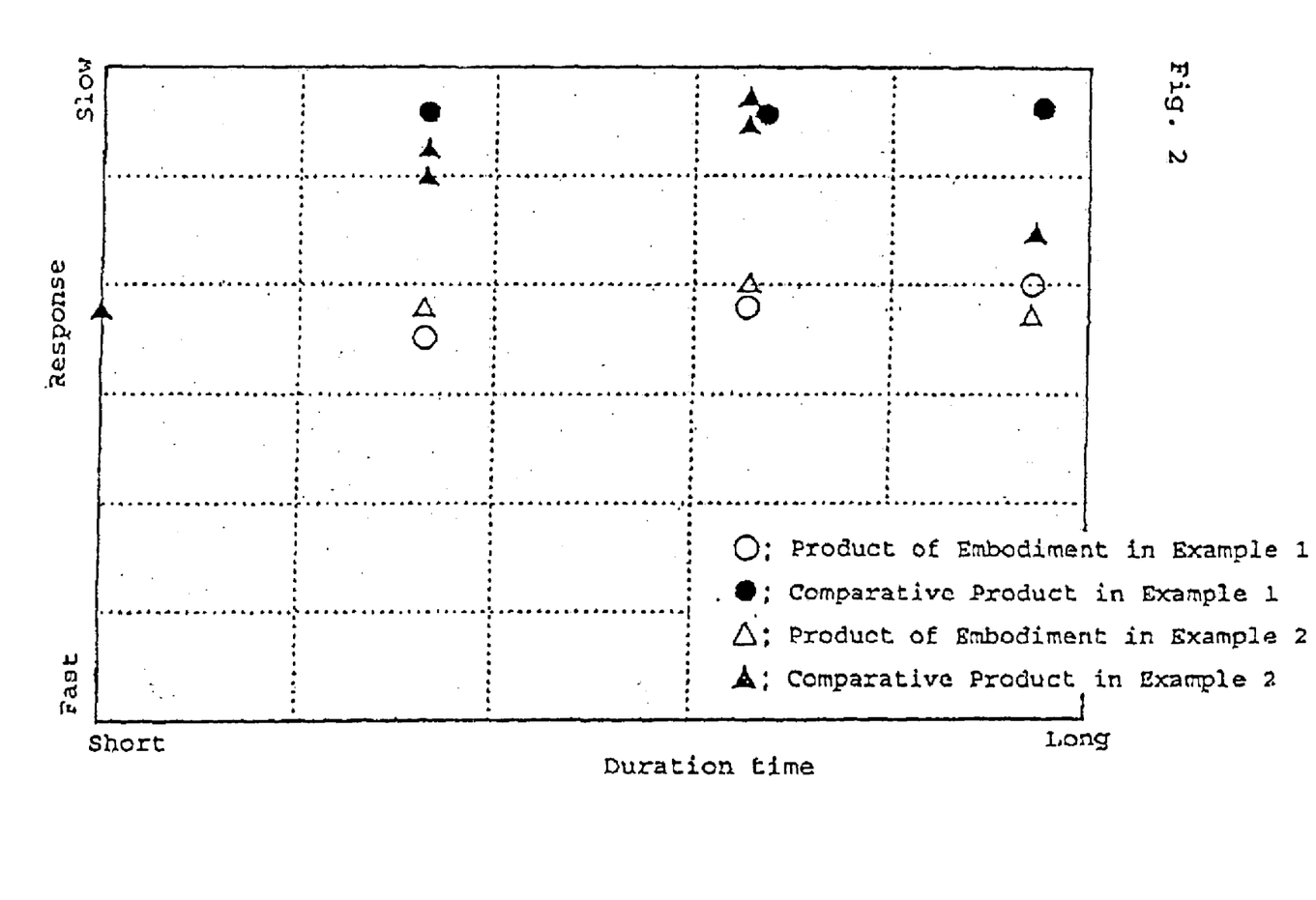
FIG. 2 is a graph illustrating that the oxygen sensor of Example 2 is excellent in durability.

The contamination preventive layer thus formed was smooth and cracks were not observed at all. Then, it was observed that the contamination preventive layer was formed in such a state that the surface of the coarse powder was sufficiently covered with the fine powders, and further that hollows of a similar size to that of the coarse powder were scattered in the inside of the contamination preventive layer. Further, as a result of evaluation in the same manner as in (2), ②, it was confirmed that although cracks due to thermal shrinkage were observed partially, it had durability capable of being put to for practical use. Further, an oxygen sensor incorporated with the sensor device having the contamination preventive layer (product of the embodiment) or an oxygen sensor incorporated with a sensor device formed with a contamination preventive layer using titania powder not containing fine grain powder (Experimental Example 2 in Table 1) (comparative product) were exposed to exhaust gases formed from fuels with addition of a predetermined amount of silicon for a long period of time and then the sensors were attached to an engine and evaluated for the response. As a result, as shown in FIG. 2, it was found that while the response was lowered considerably with lapse of time in the comparative product, delay in the response was reduced in the product of the embodiment. Further, according to the X-ray powder diffraction pattern for the contamination preventive layer, crystal phases for the anatase type titania and the rutile type titania were observed.

Figure 3:
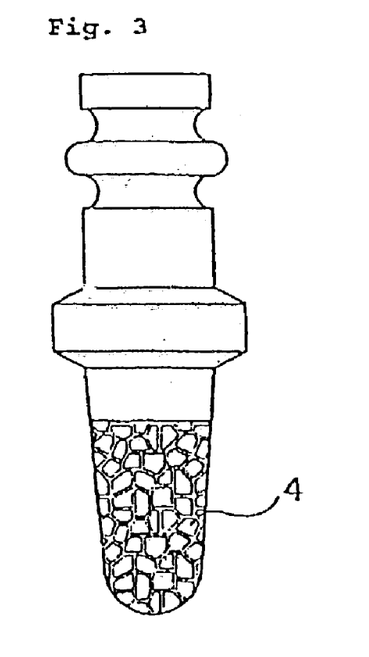
FIG. 3 is a front elevation al view illustrating an appearance after forming an electrode protection layer of the sensor device.
Figure 4:
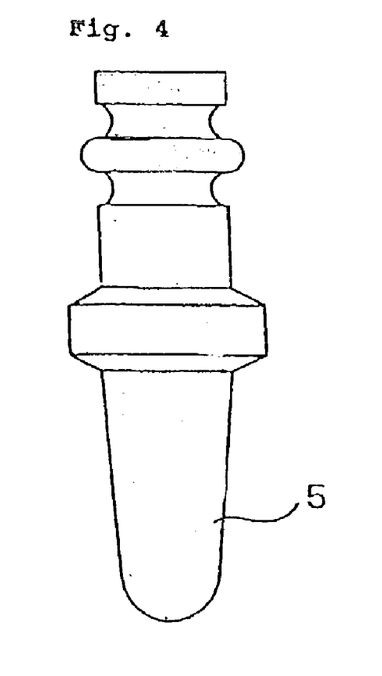
FIG. 4 is a front elevational view illustrating an appearance after forming the contamination preventive layer.
Figure 5:
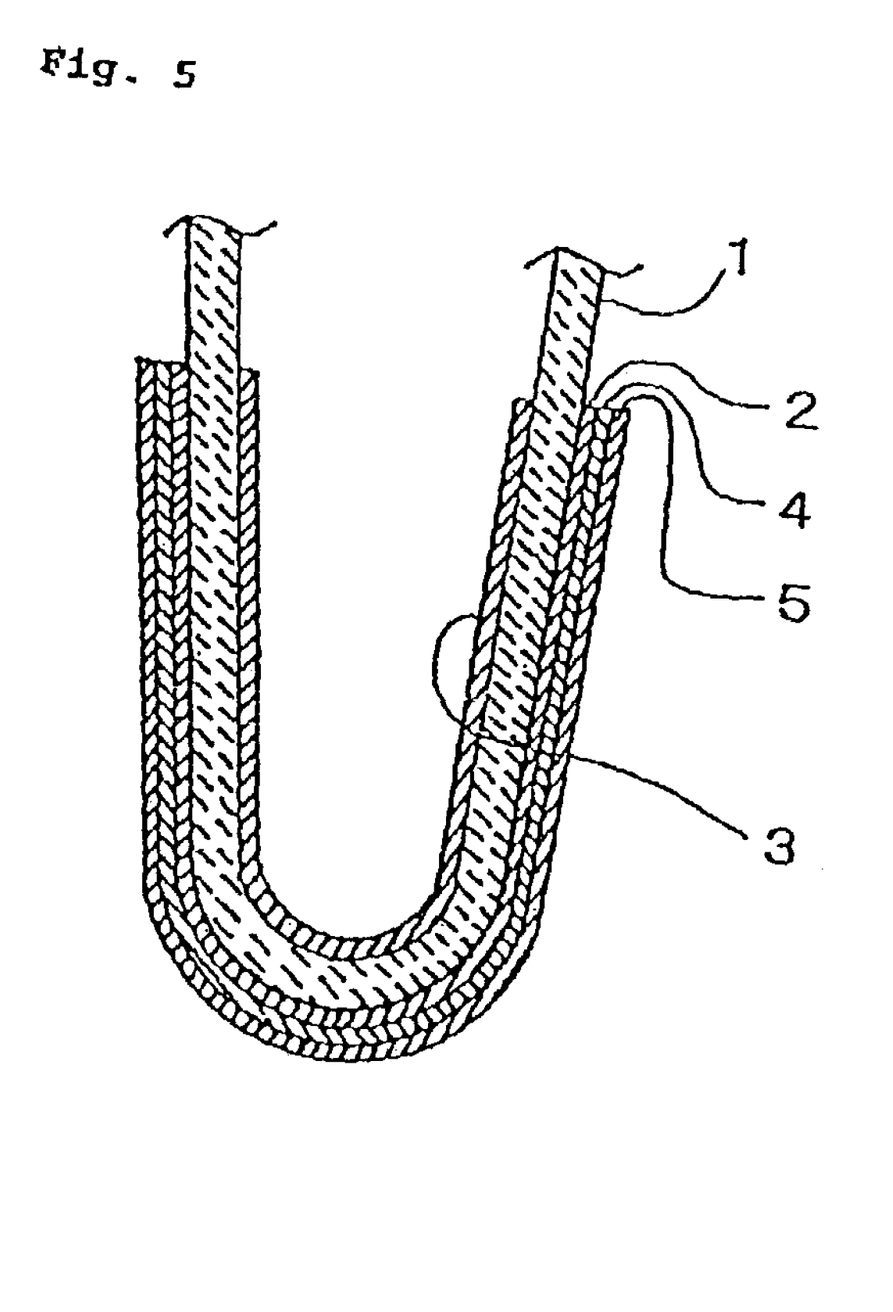
FIG. 5 is a cross sectional view of a sensor device in which a detection electrode or the like is formed on the outer surface and a reference electrode is formed on the inner surface of a solid electrolyte substrate of the sensor device.

FIG. 3 shows an appearance of the sensor device of Examples 1 and 2 after forming the electrode protection layer. Further, FIG. 4 illustrates an appearance after forming the contamination preventive layer. Further, FIG. 5 illustrates a cross section for a portion where the electrode, the electrode protection layer and the contamination preventive layer are formed. As shown in FIG. 5, the sensor device comprises a solid electrolyte substrate 1, as well as a detection electrode 2, an electrode protection layer 4 and a contamination preventive layer 5 formed successively to the outer surface thereof, and a reference electrode 3 formed on the inner surface. Further, this invention is applicable to a sensor having a solid electrolyte substrate in the shape of a plate-shaped lamination type in addition to the cylindrical type.

This invention is not restricted to those shown by the specific examples described above but may be variously modified into examples within a range of this invention in accordance with the purpose and the application use. That is, the specific surface area of the ceramic powder such as titania and the thickness and porosity of the contamination preventive layer can be adjusted optionally. Further, the detection electrode and the reference electrode are not always formed over the entire surface at the bottom circumference of the solid electrolyte substrate but they may be a band-like shape. Further, a protection layer of the composition identical with that of the electrode protection layer may be formed further to the surface of the contamination preventive layer.

Effects of the Invention

According to this invention, since the contamination preventive layer containing a fine ceramic powder having a specified grain size and a ceramic powder having a relatively large grain size and a narrow grain size distribution is formed, the contamination can be prevented efficiently particularly even when it is in contact with contamination substances such as lead contained in exhaust gases at a low temperature, and the contamination preventive layer is less exfoliated from the electrode protection layer and an oxygen sensor of excellent performance with less change in response can be obtained. Further, by using the contamination preventive layer forming paste containing ceramic powders of different specific surface areas, an oxygen sensor can be manufactured easily.

What is claimed is:

1. An oxygen sensor comprising:
   a solid electrolyte substrate;
   a detection electrode formed on the surface of the solid electrolyte substrate;
   an electrode protection layer formed on the surface of the detection electrode; and
   a contamination preventive layer formed on the surface of the electrode protection layer and comprising large ceramic grains and small ceramic grains adhered to the large ceramic grains; and
   hollows scattered in the contamination prevention layer;
   wherein the small ceramic grains differ in material from the large ceramic grains,
   wherein a grain-size distribution peak of the large ceramic grains is 1-50 μm,
   wherein a grain-size distribution peak of the small ceramic grains is about 0.003-1 μm, and
   wherein each of the hollows is about 1-50 μm.

2. The oxygen sensor according to claim 1, wherein the grain-size distribution peak of the small ceramic grains is about 0.0003-0.5 μm.

3. The oxygen sensor according to claim 1, wherein a material of the small ceramic grains is titania and a material of the large ceramic grains is one of spinel or mullite.

* * * * *